(12) United States Patent
Wu et al.

(10) Patent No.: US 11,436,732 B2
(45) Date of Patent: Sep. 6, 2022

(54) AUTOMATIC SEGMENTATION OF ACUTE ISCHEMIC STROKE LESIONS IN COMPUTED TOMOGRAPHY DATA

(71) Applicant: The General Hospital Corporation, Boston, MA (US)

(72) Inventors: Ona Wu, Charlestown, MA (US); Ramon Gilberto Gonzalez, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 25 days.

(21) Appl. No.: 16/817,551

(22) Filed: Mar. 12, 2020

(65) Prior Publication Data

US 2020/0294241 A1    Sep. 17, 2020

Related U.S. Application Data

(60) Provisional application No. 62/817,006, filed on Mar. 12, 2019.

(51) Int. Cl.
*G06K 9/00* (2022.01)
*G06T 7/10* (2017.01)
(Continued)

(52) U.S. Cl.
CPC .............. *G06T 7/10* (2017.01); *G06K 9/6256* (2013.01); *G06N 3/084* (2013.01); *G06N 20/00* (2019.01);
(Continued)

(58) Field of Classification Search
CPC ..................... G06T 7/10; G06T 7/0012; G06T 2207/20081; G06T 2207/10081;
(Continued)

(56) References Cited

U.S. PATENT DOCUMENTS

2014/0056842 A1* 2/2014 Sackner-Bernstein ....................... A61K 38/19
424/85.1
2014/0062477 A1* 3/2014 Carroll ............. G01R 33/56366
324/309

(Continued)

OTHER PUBLICATIONS

Liu P. Stroke Lesion Segmentation with 2D Novel CNN Pipeline and Novel Loss Function. In: Crimi A.,Bakas S., Kuijf H., Keyvan F., Reyes M., van Walsum T. (eds) Brainlesion: Glioma, Multiple Sclerosis, Stroke and Traumatic Brain Injuries. BrainLess 2018. Lecture Notes in Computer Sciences, vol. 11383. (Year: 2018).*

(Continued)

*Primary Examiner* — Van D Huynh
(74) *Attorney, Agent, or Firm* — Quarles & Brady LLP

(57) ABSTRACT

Lesions associated with acute ischemic stroke are automatically segmented in images acquired with computed tomography ("CT") using a trained machine learning algorithm (e.g., a neural network). The machine learning algorithm is trained on labeled data and associated CT data (e.g., non-contrast CT data and CT angiography source image ("CTA-SI") data). The labeled data can include segmented data indicating lesions, which are generated by segmenting diffusion-weighted magnetic resonance images acquired within a specified time window from when the associated CT data were acquired. CT data (e.g., non-contrast CT data and CTA-SI data) acquired from a subject are then acquired and input to the trained machine learning algorithm to generate output as segmented CT data, which indicate lesions in the subject.

15 Claims, 11 Drawing Sheets

(51) Int. Cl.
  *G06T 7/00* (2017.01)
  *G06N 3/08* (2006.01)
  *G06N 20/00* (2019.01)
  *G16H 30/40* (2018.01)
  *G06K 9/62* (2022.01)

(52) U.S. Cl.
  CPC ........... *G06T 7/0012* (2013.01); *G16H 30/40* (2018.01); *G06T 2207/10081* (2013.01); *G06T 2207/20081* (2013.01); *G06T 2207/20084* (2013.01); *G06T 2207/30096* (2013.01)

(58) Field of Classification Search
  CPC . G06T 2207/30096; G06T 2207/20084; G06T 2207/30016; G06T 7/11; G06N 3/084; G06N 20/00; G06N 3/0454; G16H 30/40; G16H 50/20; G06K 9/6256; G06K 9/6273; G06K 2209/05
  USPC ......................................................... 382/128
  See application file for complete search history.

(56) References Cited

U.S. PATENT DOCUMENTS

| | | | |
|---|---|---|---|
| 2017/0023658 A1* | 1/2017 | Sun | A61B 5/055 |
| 2018/0136297 A1* | 5/2018 | Koch | G01R 33/56536 |
| 2019/0026888 A1* | 1/2019 | Beveridge | A61B 6/481 |
| 2019/0320896 A1* | 10/2019 | Kassab | A61B 3/1241 |
| 2019/0391222 A1* | 12/2019 | Majumdar | G16H 30/20 |
| 2020/0143571 A1* | 5/2020 | Bagherzadeh | G06T 11/003 |

OTHER PUBLICATIONS

Öman, O., Mäkelä, T., Salli, E. et al. 3D convolutional neural networks applied to CT angiography in the detection of acute ischemic stroke. Eur Radiol Exp 3, 8 (2019). https://doi.org/10.1186/s41747-019-0085-6 (Year: 2019).*

Chen et al., Fully Automatic Acute Ischemic Lesion Segmentation in DWI Using Convolutional Neural Networks, NeuroImage: Clinical, 2017, 15:633-643.

Copen et al., In Patients with Suspected Acute Stroke, CT Perfusion-Based Cerebral Blood Flow Maps Cannot Substitute for DWI in Measuring the Ischemic Core, PloS One, 2017, 12(11):e0188891, 20 pages.

Hevia-Montiel et al., Robust Nonparametric Segmentation of Infarct Lesion from Diffusion-Weighted MR Images, Proceedings of the 29th Annual International Conference of the IEEE Engineering in Medicine and Biology Society, 2007, pp. 2102-2105.

Jacobs et al., Multi parametric MRI Tissue Characterization in Clinical Stroke with Correlation to Clinical Outcome: Part 2, Stroke, 2001, 32(4):950-957.

Kamnitsas et al., Efficient Multi-Scale 3D CNN with Fully Connected CRF for Accurate Brain Lesion Segmentation, Medical Image Analysis, 2017, 36:61-78.

Kamnitsas et al., Ensembles of Multiple Models and Architectures for Robust Brain Tumour Segmentation, MICCAI BrainLes, 2017, 12 pages.

Luby et al., Intra-and Interrater Reliability of Ischemic Lesion Volume Measurements on Diffusion-Weighted, Mean Transit Time and Fluid-Attenuated Inversion Recovery MRI, Stroke, 2006, 37(12):2951-2956.

Maier et al., ISLES 2015—A Public Evaluation Benchmark for Ischemic Stroke Lesion Segmentation from Multispectral MRI, Medical Image Analysis, 2017, 35:250-269.

Mujumdar et al., A Novel Framework for Segmentation of Stroke Lesions in Diffusion Weighted MRI Using Multiple b-Value Data, In Proceedings of the 21st International Conference on Pattern Recognition, 2012, pp. 3762-3765.

Sorensen et al., Human Acute Cerebral Ischemia: Detection of Changes in Water Diffusion Anisotropy by Using MR Imaging, Radiology, 1999, 212(3):785-792.

Straka et al., Real-Time Diffusion-Perfusion Mismatch Analysis in Acute Stroke, Journal of Magnetic Resonance Imaging, 2010, 32(5):1024-1037.

Tsai et al., Automatic Detection and Quantification of Acute Cerebral Infarct by Fuzzy Clustering and Histographic Characterization on Diffusion Weighted MR Imaging and Apparent Diffusion Coefficient Map, BioMed Research International, 2014, vol. 2014, Article ID 963032, 13 pages.

Winzeck et al., Ensemble of Convolutional Neural Networks Improves Automated Segmentation of Acute Ischemic Lesions Using Multiparametric Diffusion-Weighted MRI, American Journal of Neuroradiology, 2019, 40(6):938-945.

Wu et al., Predicting Tissue Outcome in Acute Human Cerebral Ischemia Using Combined Diffusion-and Perfusion-Weighted MR Imaging, Stroke, 2001, 32(4):933-942.

Wu et al., Using MRI as the Witness: Multimodal MRI-Based Determination of Acute Stroke Onset, Stroke, 2010, 41(4):E273-E273.

Wu et al., Abstract 3319: Prediction of Lesion Expansion in Stroke Patients Using Acute MRI, Stroke, 2012, vol. 43, Issue Suppl_1, A3319.

Yoshiura et al., Highly Diffusion-Sensitized MRI of Brain: Dissociation of Gray and White Matter, Magnetic Resonance in Medicine, 2001, 45(5):734-740.

Zhang et al., Automatic Segmentation of Acute Ischemic Stroke from DWI Using 3-D Fully Convolutional DenseNets, IEEE Transactions on Medical Imaging, 2018, 37(9):2149-2160.

* cited by examiner

AUTOMATIC SEGMENTATION OF ACUTE ISCHEMIC STROKE LESIONS IN COMPUTED TOMOGRAPHY DATA

CROSS-REFERENCE TO RELATED APPLICATIONS

This application claims the benefit of U.S. Provisional Patent Application Ser. No. 62/817,006, filed on Mar. 12, 2019, and entitled "Pragmatic lesion segmentation of acute ischemic stroke CT scans," which is herein incorporated by reference in its entirety.

BACKGROUND

Most hospitals do not have access to the advanced imaging equipment that were used in recent clinical trials that used imaging to expand the therapeutic time window for thrombolysis and endovascular therapy, but instead must rely on CT scans for routine diagnostic workup. Less than 20% of all academic stroke centers have the capability to perform MRI acutely. As an alternative to identifying tissue infarction on MRI using diffusion-weighted imaging (also known as the infarct "core"), many centers have chosen to use CT perfusion imaging ("CTP"), where very low cerebral blood flow values are used instead to identify severely injured brain tissue. However, calculation of cerebral blood flow requires expensive software, experts to set up the CTP protocol, injection of contrast agents that can induce nephropathy and extensive exposure to radiation. Most hospitals lack access to either MRI or advanced software in the acute setting.

In addition, CBF-based "cores" have been shown to be inaccurate since they do not represent tissue infarction but low flow that can renormalize with reperfusion, and their use may deny treatment to patients who may otherwise benefit from intervention. Other approaches utilize an ASPECTS score threshold, e.g. >7 to determine extend of early ischemic injury. Qualitative assessments can vary by reader. There are efforts to create automatic ASPECTS score using machine learning by several companies. However, the ASPECTS score focuses on infarction involving the middle cerebral artery territory, while injury to other vascular territories are largely ignored.

SUMMARY OF THE DISCLOSURE

The present disclosure addresses the aforementioned drawbacks by providing a method for automatically generating a segmented image of an acute stroke patient using computed tomography (CT) data. The method includes accessing CT data of a subject and accessing a trained machine learning algorithm with the computer system. The CT data can include both non-contrast CT data and CT angiography source image (CTA-SI) data. The trained machine learning algorithm has been trained using labeled data and associated CT imaging data in order to segment acute ischemic stroke lesions. The labeled data are generated based on diffusion-weighted magnetic resonance images. Segmented CT data are generated with the computer system by inputting the CT data to the trained machine learning algorithm, generating output as the segmented CT data. The segmented CT data can then be displayed to a user.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are systems and methods for segmenting lesions associated with acute ischemic stroke in images acquired with computed tomography ("CT") using a machine learning algorithm, such as a neural network, that has been trained on labeled data and associated CT data. As an example, the labeled data are generated by segmenting acute ischemic stroke lesions from diffusion-weighted imaging ("DWI") data that have been acquired relatively close in time after CT scans (e.g., non-contrast CT data, CT angiography data). These labeled data and the associated CT data are used to train the machine learning algorithm for acute ischemic stroke segmentation using co-registered non-contrast CT and CT angiography ("CTA") data sets.

Advantageously, the systems and methods described in the present disclosure can improve patient triage, particularly at hospitals and in clinical settings that do not have access to advanced imaging technologies, by identifying the likelihood of whether a patient will respond to revascularization treatment. The systems and methods described in the present disclosure are able to automatically quantify the extent of dead brain tissue using acute non-contrast CT and CTA-SI data.

Figure 1:
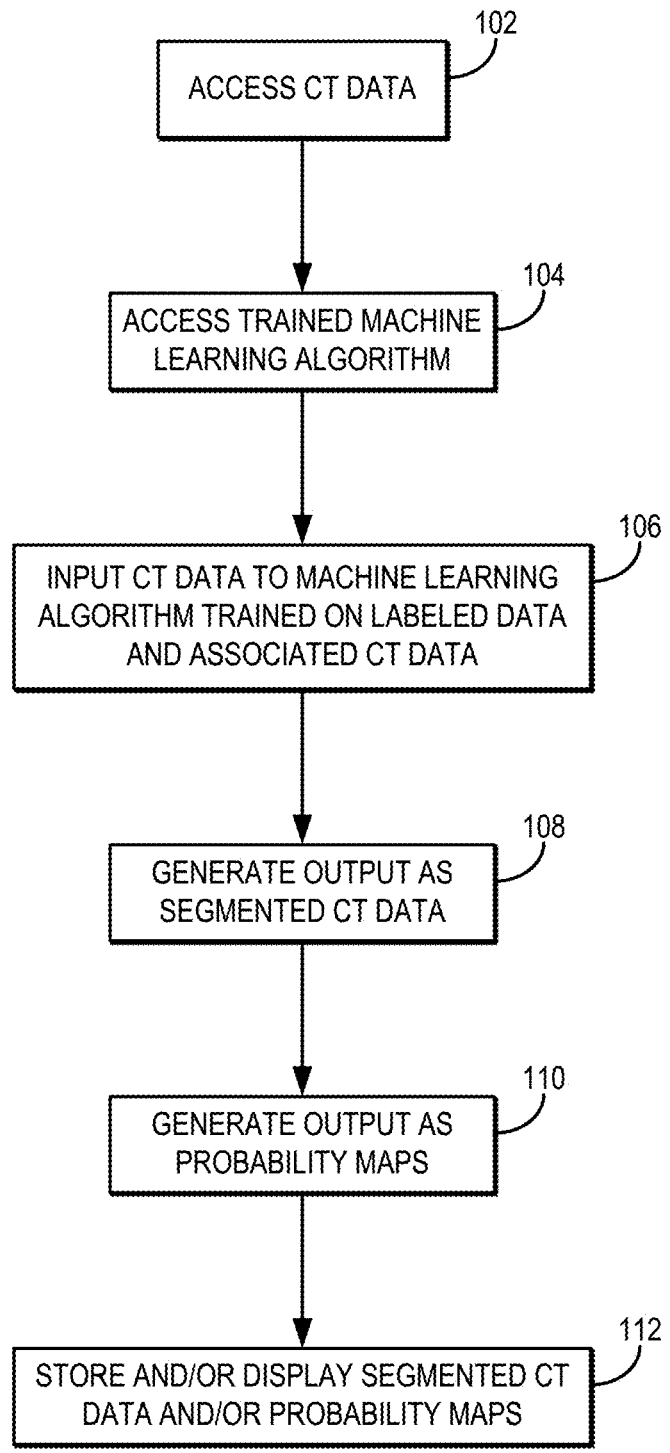
FIG. 1 is a flowchart setting forth the steps of an example method for automatically segmenting and classifying acute ischemic stroke lesions based on CT data and using a machine learning algorithm trained on multiparametric MRI data and associated CT data.

Referring now to FIG. 1, a flowchart is illustrated as setting forth the steps of an example method for automatically segmenting and/or classifying brain regions as corresponding to acute ischemic stroke lesions by inputting CT data to a suitably trained machine learning algorithm.

The method includes accessing CT data with a computer system, as indicated at step 102. Accessing these data can include retrieving previously acquired data from a memory or other suitable data storage device or medium. Additionally or alternatively, accessing these data can include acquiring data with a CT imaging system and communicating or otherwise transferring the data to the computer system, which may be a part of the CT imaging system. In general, the CT data include both non-contrast CT data and CTA data. For instance, CTA data can include CTA source image ("CTA-SI") data.

A trained machine learning algorithm (e.g., a neural network) is then accessed with the computer system, as indicated at step 104. Accessing a trained neural network may include accessing network parameters (e.g., weights, biases, or both) that have been optimized or otherwise estimated by training the neural network on training data. In some instances, retrieving a neural network can also include retrieving, constructing, or otherwise accessing the particular neural network architecture to be implemented. For instance, data pertaining to the layers in the neural network architecture (e.g., number of layers, type of layers, ordering of layers, connections between layers, hyperparameters for layers) may be retrieved, selected, constructed, or otherwise accessed.

In general, the neural network is trained, or has been trained, on training data that includes labeled data and associated CT data. As will be described in more detail below, the labeled data generally include diffusion-weighted imaging ("DWI") data that have been acquired with an MRI system and segmented manually, semi-automatically, or automatically to identify lesions within the images. The associated CT data include non-contrast CT and/or CTA data acquired within a certain time from when the DWI data were acquired.

The CT data are then input to the trained machine learning algorithm, as indicated at step 106, generating output as segmented CT data, as indicated at step 108, as probability maps, as indicated at step 110, or both. For instance, the output may be generated such that one output channel of the machine learning algorithm corresponds to the segmented CT data and another output of the machine learning algorithm corresponds to the probability map. Other quantitative data may also be output or computed, such as lesion volume.

As one example, the machine learning algorithms may be implemented as a neural network. The neural network may be a convolutional neural network, a residual neural network, or other suitable type of neural network. In some instances, the neural network may be implemented with deep learning. As one non-limiting example, the neural network can be a multi-scale 3D deep convolutional neural network. In some implementations, the neural network may include an attention network, such as a domain attention network.

Figure 2A:
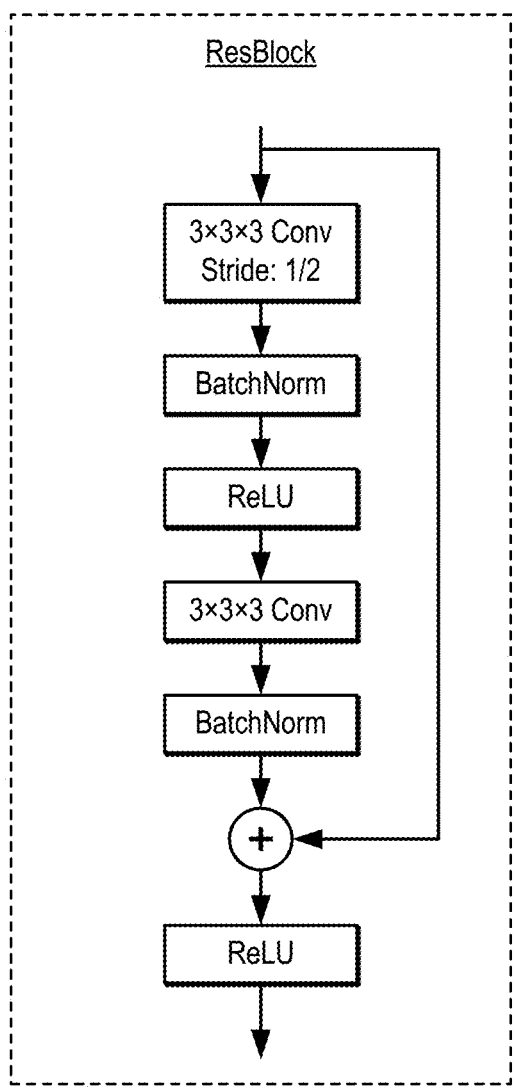
FIG. 2A is an example of a ResBlock that can be used in a residual neural network ("ResNet").
Figure 2B:
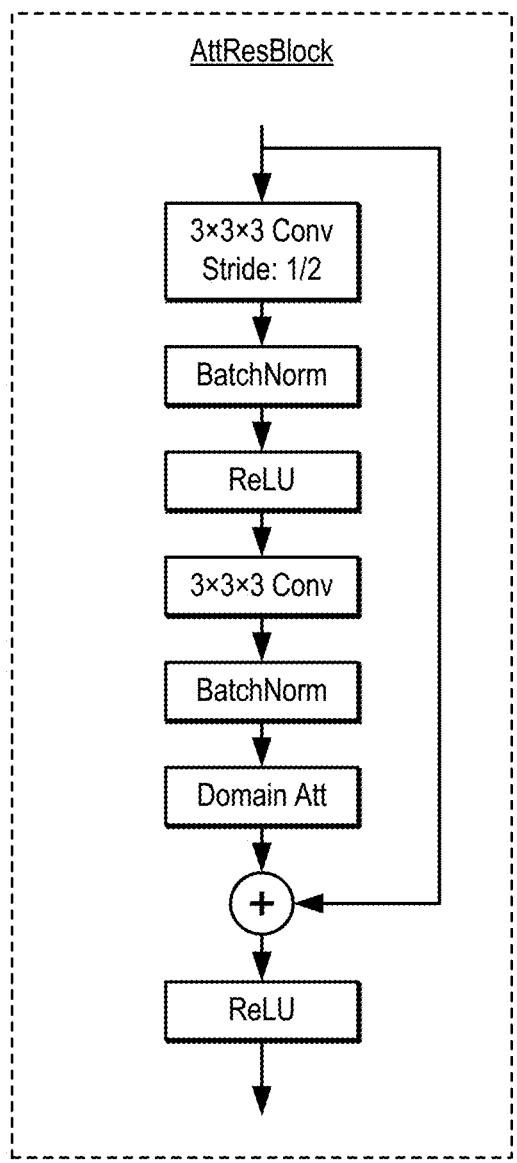
FIG. 2B is an example of a ResBlock that incorporates a domain attention network ("AttResBlock), which can be used in a ResNet.
Figure 2C:
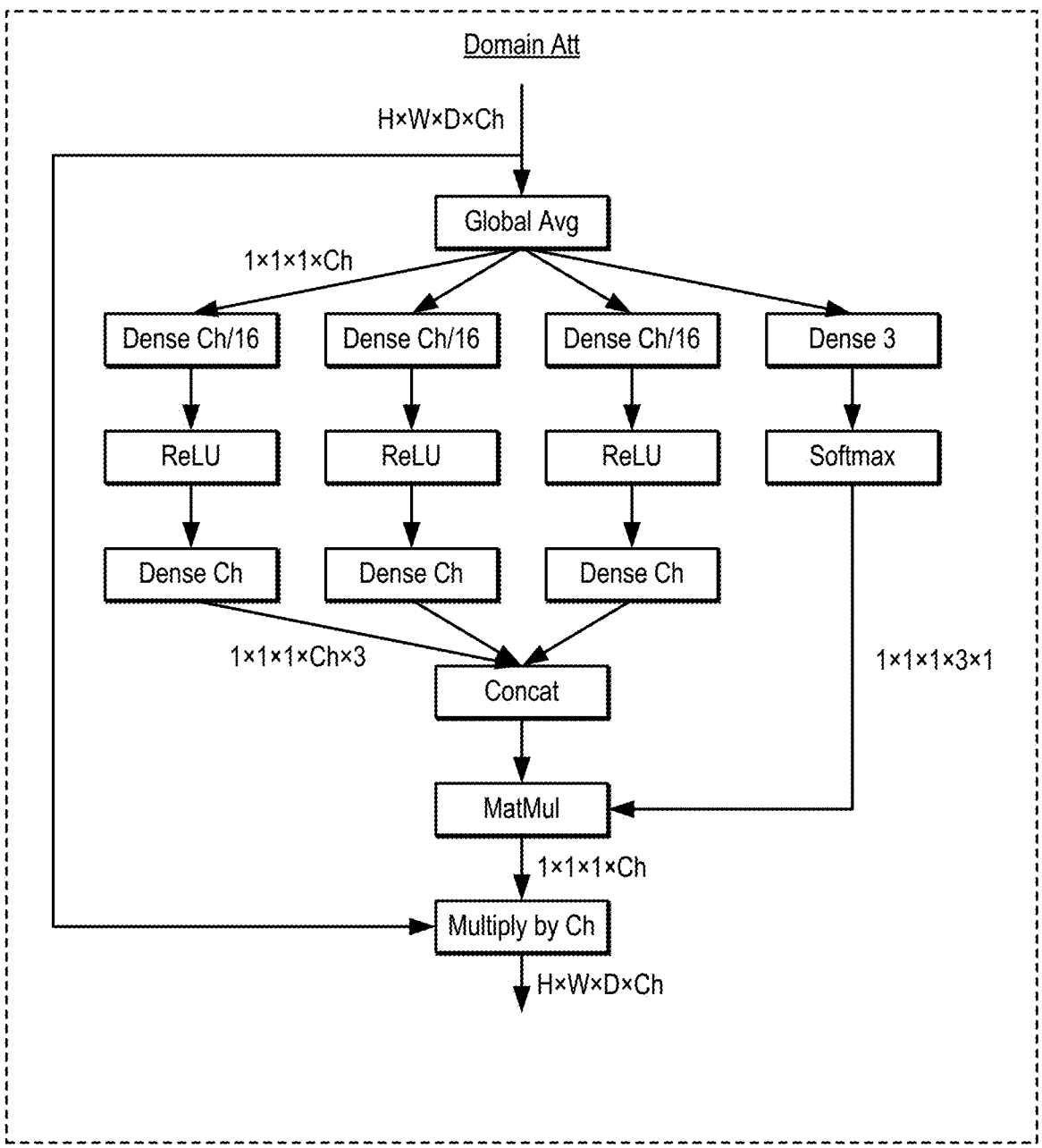
FIG. 2C is an example of a domain attention network ("Domain Att") that can be used in an AttResBlock.
Figure 2D:
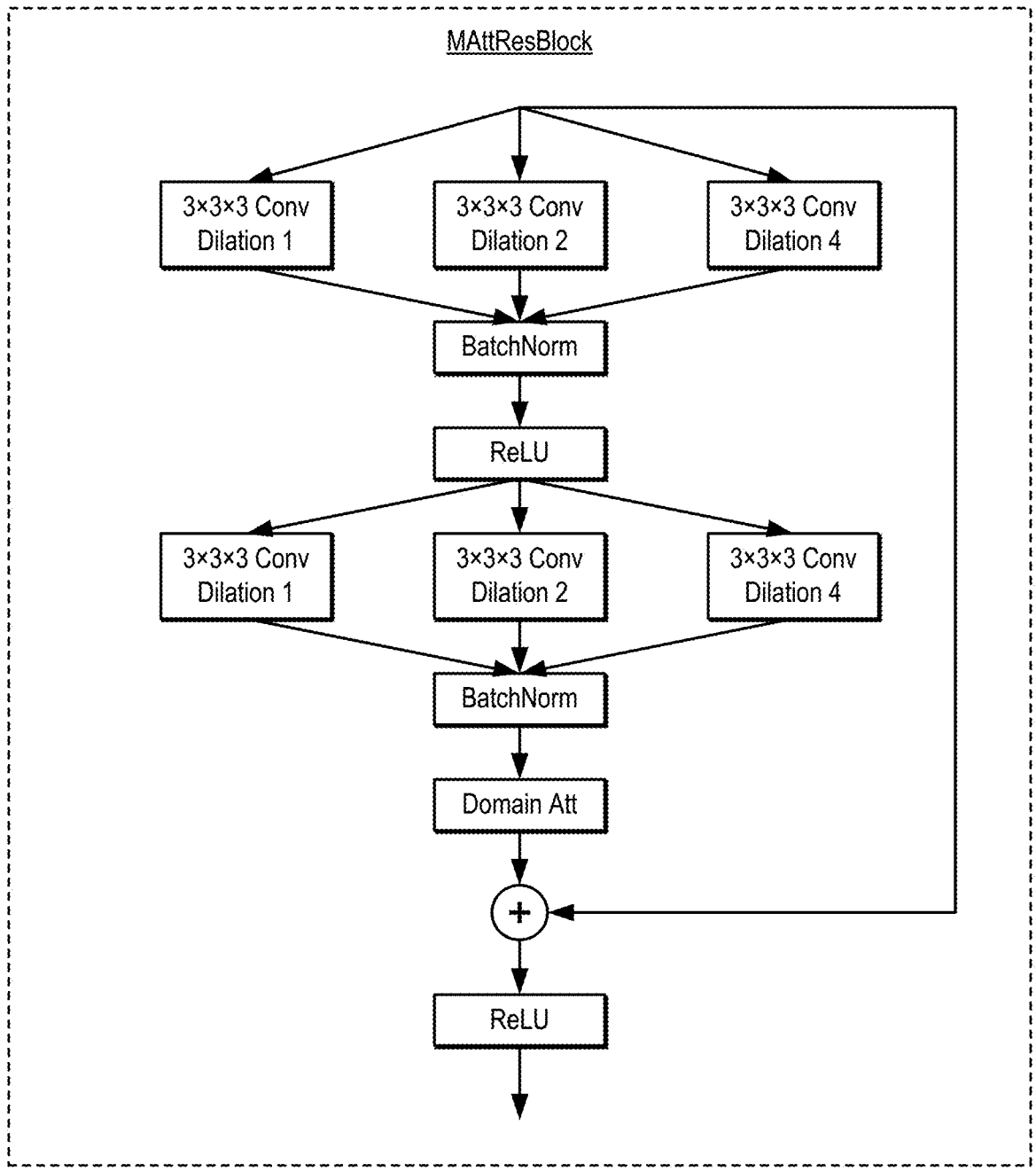
FIG. 2D is an example of a multi-scale AttResBlock ("MAttResBlock"), which can be used in a ResNet.
Figure 2E:
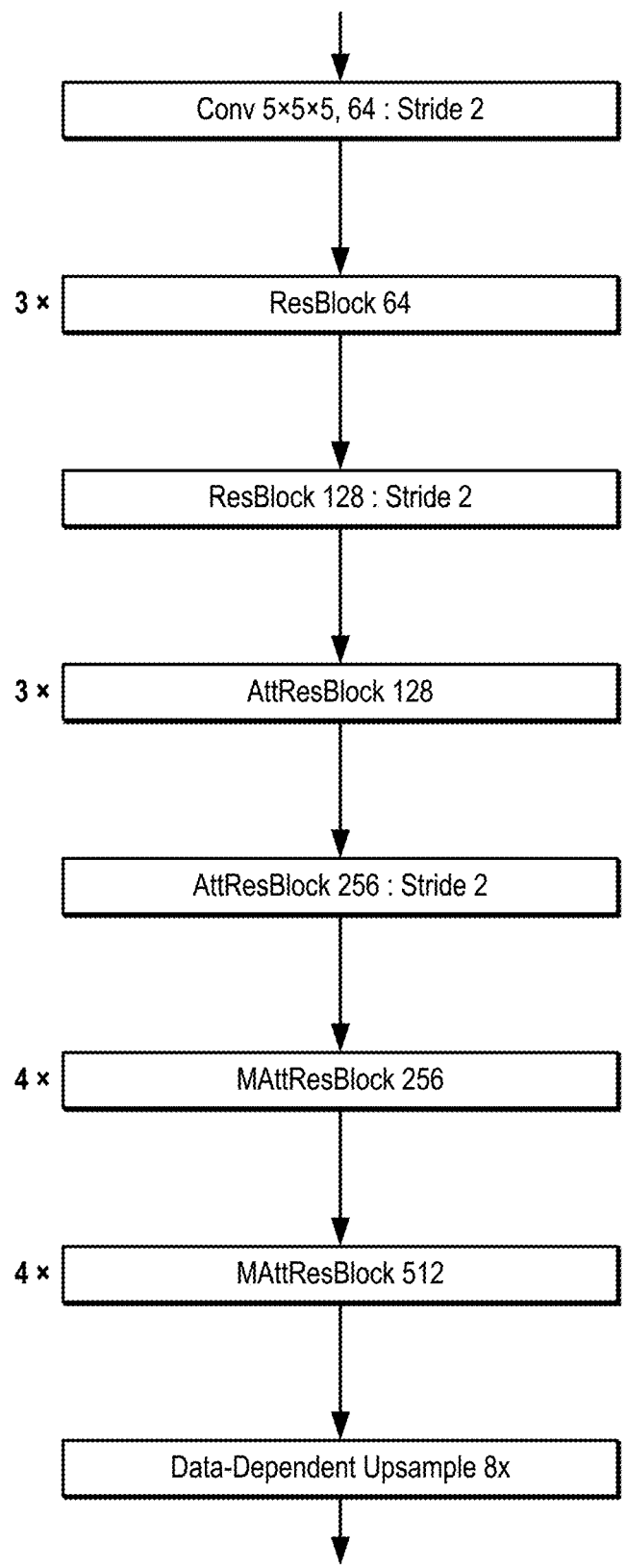
FIG. 2E is an example of a ResNet that includes ResBlock, AttResBlock, and MAttResBlock layers.

As a non-limiting example, the neural network can be a residual neural network ("ResNet") that may include a domain attention network. An example of a residual block ("ResBlock") that can be used in a ResNet is shown in FIG. 2A. An example of a ResBlock that includes a domain attention network ("AttResBlock") is shown in FIG. 2B. An example of a domain attention network ("Domain Att") is shown in FIG. 2C. An example of a multi-scale AttResBlock is shown in FIG. 2D. One or more of these blocks may be used in a ResNet, such as the ResNet shown in FIG. 2E.

In some embodiments, the machine learning algorithm, which may be implemented as a neural network, can be trained for acute ischemic stroke lesion segmentation tasks. For example, an output channel of such a machine learning algorithm can predict a classification for each portion of the input data as lesion versus non-lesion (e.g., a probability that a segmented voxel corresponds to infarct). In some embodiments, additional post-processing techniques (e.g., thresholding) can be applied on the predicted probabilities for lesion segmentation.

As indicated at step 110, the automatically segmented image(s) or other quantitative maps or data (e.g. infarct probability maps, quantified lesion volume) can be stored and/or displayed to a user, indicating the location of one or more lesions identified by the trained machine learning algorithm. For example, an image similar to the segmentation images, probability maps, or both, shown in FIGS. 3A and 3B can be presented to a user based on the output of the trained machine learning algorithm.

Figure 3A:
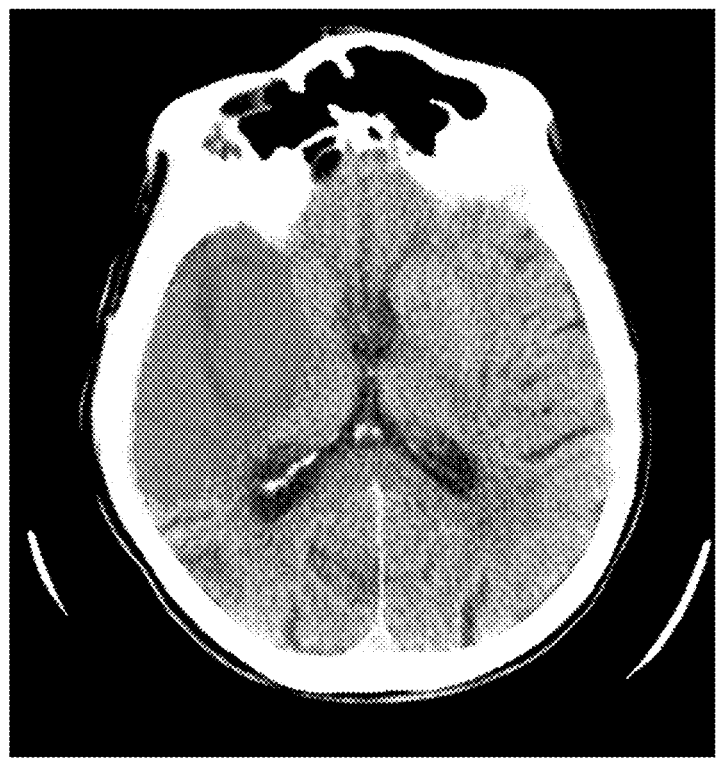
FIG. 3A is an example of segmented CT data that can be generated using the methods described in the present disclosure.
Figure 3B:
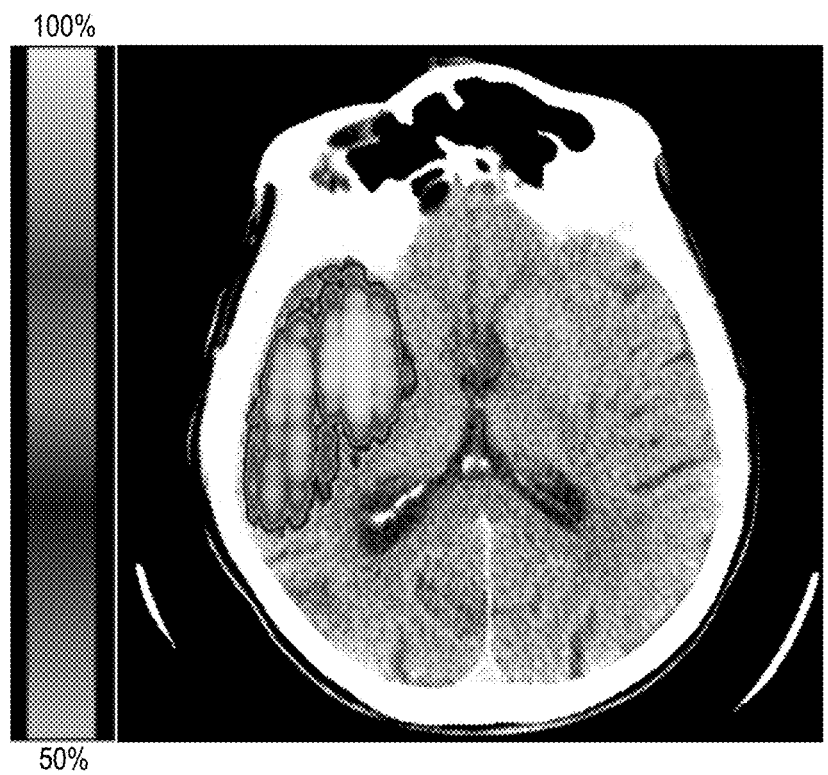
FIG. 3B is an example of a lesion probability map that can be generated using the methods described in the present disclosure.

The images in FIGS. 3A and 3B depict example segmentation results of inputting CT data to a trained machine learning algorithm in accordance with some embodiments described in the present disclosure. FIG. 3A is an example of segmented CT data, which depicts a CT image having displayed thereon a region associated with a segmented region. Alternatively, the segmented CT data can include just the segmentation mask associated with lesion. FIG. 3B is an example of a lesion probability map, which depicts a probability that tissues are associated with a lesion, such as an acute infarct. In this instance, the probability map includes probability values that are overlaid on top of a CT image, such that the probability values are spatially associated with the underlying tissue regions.

The presented segmented images can be used by the user to inform a diagnosis, and/or to help make decisions about whether further tests are likely to be useful. In some embodiments, the segmentation can be presented to indicate the presence of a clinically significant lesion and a location at which the lesion is likely to be located. In some embodiments, information about a predicted lesion classification that is generated by the machine learning algorithm can be omitted from presentation with the segmentation information. For example, the segmentation can be presented with similar visual characteristics (e.g., using the same color) regardless of the underlying likelihood that the lesion corresponds to a particular classification. In such an example, the segmentation can indicate the extent of a predicted clinically significant lesion.

Alternatively, in some embodiments, information about the predicted likelihood of classification can be presented in connection with the segmentation and/or separately from the segmentation. For example, in some embodiments, the segmentation can be visualized in connection with a probability map based on the output from a particular output channel of the trained machine learning algorithm. As another example, the segmentation can be presented in a color or pattern that represents a probability of infarct at each voxel within the segmented region(s). In some embodiments, information presented at step 110 can be provided to allow a user to make a more informed decision about whether to perform an intervention on the patient, the urgency of performing an intervention, and so on.

Figure 4:
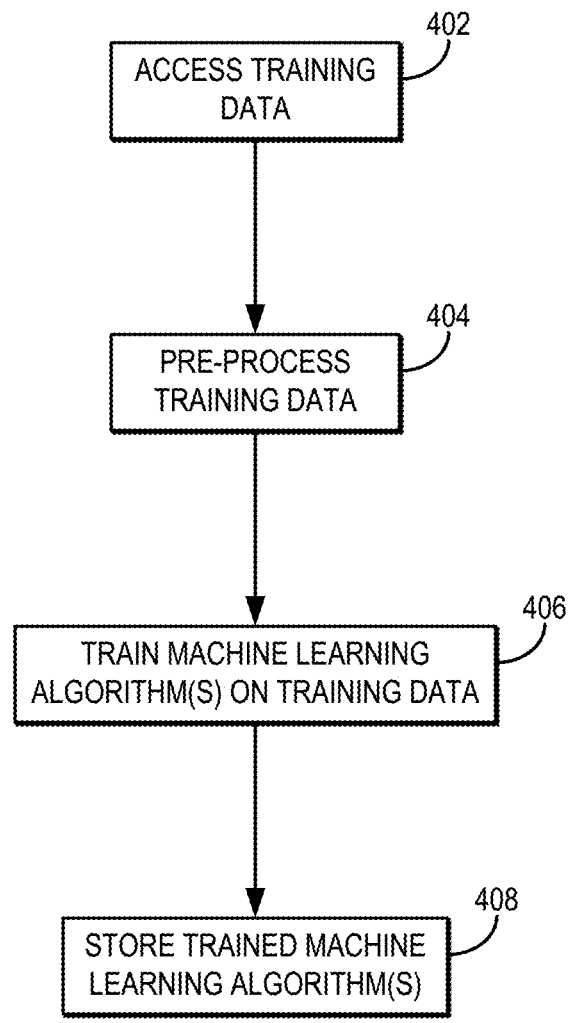
FIG. 4 is a flowchart setting forth the steps of an example method for training a machine learning algorithm, or ensembles thereof, to automatically segment and classify acute ischemic stroke lesions from CT data.

Referring now to FIG. 4, a flowchart is illustrated as setting forth the steps of an example method for training a machine learning algorithm to perform segmentation and/or quantification of ischemic areas in CT images.

The method includes accessing training data with a computer system, as indicated at step 402. Accessing these data can include retrieving previously acquired data from a memory or other suitable data storage device or medium. Additionally or alternatively, accessing these data can include acquiring data with a suitable medical imaging system and communicating or otherwise transferring the data to the computer system.

Figures 5A, 5B, 5C:
FIG. 5A is an example of a non-contrast CT image, which may be a part of training data used to train a machine learning algorithm, such as a neural network, to segment lesions in CT data.
FIG. 5B is an example of a CTA source image acquired from the same subject as FIG. 5A, which may be a part of training data used to train a machine learning algorithm, such as a neural network, to segment lesions in CT data.
FIG. 5C is an example of a diffusion-weighted magnetic image, acquired from the same subject as FIGS. SA and SB and within a specified time window after the CT images were acquired, which may be segmented to generate labeled data to be used as part of training data used to train a machine learning algorithm, such as a neural network, to segment lesions in CT data.

In general, the training data include both labeled data and associated CT data, which are co-registered with each other. The labeled data are generated from DWI data acquired with an MRI system. The DWI data can include diffusion-weighted images, associated diffusion parameter maps, or combinations thereof. The associated CT data can include CT angiography ("CTA") images, which may be CTA source images ("CTA-SI"). The associated CT data may in some instances also include non-contrast enhanced CT images. By co-registering the DWI data and the associated CT data, the labeled data generated from the DWI data can also be co-registered with the associated CT data, such that the regions identified in the labeled data can be spatially associated with regions in the associated CT data. FIGS. 5A-5C show examples of a non-contrast CT image (FIG. 5A), a CTA source image (FIG. 5B), and a diffusion-weighted magnetic resonance image (FIG. 5C), which was acquired 25 minutes after the non-contrast CT image and the CTA source image.

In general, each diffusion-weighted MRI data set is acquired from the same subject as the associated CT data set. The diffusion-weighted MRI data can be acquired after the CT data, and preferably within a specified time window after the CT data have been acquired. As one example, the diffusion-weighted MRI data are acquired within 24 hours of the CT data. As another example, the diffusion-weighted MRI data are acquired within 1 hour of the CT data.

The labeled data can include labeled images, such as images that have been segmented (e.g., manually segmented by a user, semi-automatically or automatically segmented with or without user validation), with the segmented regions labeled with a corresponding categorization or classification (e.g., tissue type, pathology type). In this way, the labeled data can include segmentation masks (e.g., binary images representing a segmented region).

As noted, the DWI data can be segmented manually, semi-automatically, or automatically. In some instances, the DWI data can be segmented by inputting the DWI data to a suitably trained neural network or other machine learning algorithm. As one non-limiting example, the DWI data can be segmented as described by S. Winzeck, et al., in "Ensemble of Convolutional Neural Networks Improves Automated Segmentation of Acute Ischemic Lesions Using Multiparametric Diffusion-Weighted MRI," *AJNR Am J Neuroradiol.*, 2019; 40(6):938-945, which is herein incorporated by reference in its entirety.

As one non-limiting example, the labeled images can include images in which regions have been segmented and labeled as corresponding to lesions, such as acute infarcts. The labeled images may be binary images (e.g., segmentation masks), or may include images whose pixel values are modified to correspond to a label (e.g., by changing a color mapping of the pixel values). Additionally or alternatively, segmented regions can be labeled based on the anatomical region where a lesion is located, such as one of the following categories: brainstem, cerebellum, supratentorial/cortical, or supratentorial/subcortical. The "supratentorial/cortical" designation can be used if any portion of one or more infarcts involved the cortex. Patients with both supratentorial and infratentorial lesions (i.e., lesions involving both the brainstem and cerebellum) can also be assigned to a specific category: "multiple."

Thus, in some instances, the training data can include labeled data derived from DWI data, for each subject, for slices of the associated CT data acquired from the same subject that include lesions. These labeled data indicate which portion of the associated CT data corresponds to one or more lesions, and may also indicate a class (or classes) associated with the one or more lesions. For example, the labeled data can be generated by segmenting a portion of the DWI data as corresponding to a lesion, and associating a class with the lesion, where the class indicates the anatomical location where the lesion was found, as classified by one or more experts.

In some instances, the training data can be augmented using data augmentation techniques, which may be performed before accessing the training data (i.e., the training data include augmented training data), or may be performed after accessing the training data with the computer system. As part of the data augmentation process, cloned data can be generated by making copies of the training data while altering or modifying each copy of the training data. For instance, cloned data can be generated using data augmentation techniques, such as performing a deformable transformation (e.g., flip, rotation, zoom, or combination thereof) on the original training data, and so on.

As indicated at step 404, in some embodiments, the training data can be pre-processed. For example, non-contrast CT images and CTA source images can be resampled to an isotropic voxel size (e.g., 1 mm$^3$). As another example, a CT brain mask can be computed, after which mean and standard deviation values can be calculated from intensities within the brain mask and limited to the [1, 99] percentile range to normalize values to mean 0 and standard deviation 1.0.

One or more machine learning algorithms are then trained on the training data, as indicated at step 406. As noted above, the machine learning algorithm may include a neural network, such as a convolutional neural network or other type of artificial neural network. In such instances, the neural network can be trained by optimizing network parameters (e.g., weights, biases, or both) based on minimizing a loss function. As one non-limiting example, the loss function may be a mean squared error loss function.

Training a neural network (or other machine learning algorithm) may include initializing the neural network, such as by computing, estimating, or otherwise selecting initial network parameters (e.g., weights, biases, or both). Training data can then be input to the initialized neural network, generating output as segmented CT data and/or feature maps (e.g., lesion probability maps). The quality of the output data can then be evaluated, such as by passing the output data to the loss function to compute an error. The current neural network can then be updated based on the calculated error (e.g., using backpropagation methods based on the calculated error). For instance, the current neural network can be updated by updating the network parameters (e.g., weights, biases, or both) in order to minimize the loss according to the loss function. When the error has been minimized (e.g., by determining whether an error threshold or other stopping criterion has been satisfied), the current neural network and its associated network parameters represent the trained neural network.

In one non-limiting example, a machine learning algorithm implementing CNNs, such as those shown in FIG. 3, were trained to classify voxels as lesion or non-lesion on a GPU using an Adam optimizer. In one example study, a neural network was trained over 110 epochs with a learning rate of 0.0002 for the first 80 epochs and a learning rate of 0.00002 for the last 30 epochs. The results of all models can be resampled back to the original image resolution, thresholded (e.g., thresholded at 50%), and/or masked with the resampled brain mask created at the normalization preprocessing step. Performance within the training data can be assessed using a withheld unseen test cohort.

The one or more trained machine learning algorithms, which may be neural networks, are then stored for later use, as indicated at step 408. For instance, storing neural network(s) may include storing network parameters (e.g., weights, biases, or both), which have been computed or otherwise estimated by training the neural network(s) on the training data. Storing trained neural network(s) may also include storing the particular neural network architecture to be implemented. For instance, data pertaining to the layers in the neural network architecture (e.g., number of layers, type of layers, ordering of layers, connections between layers, hyperparameters for layers) may be stored.

Figure 6:
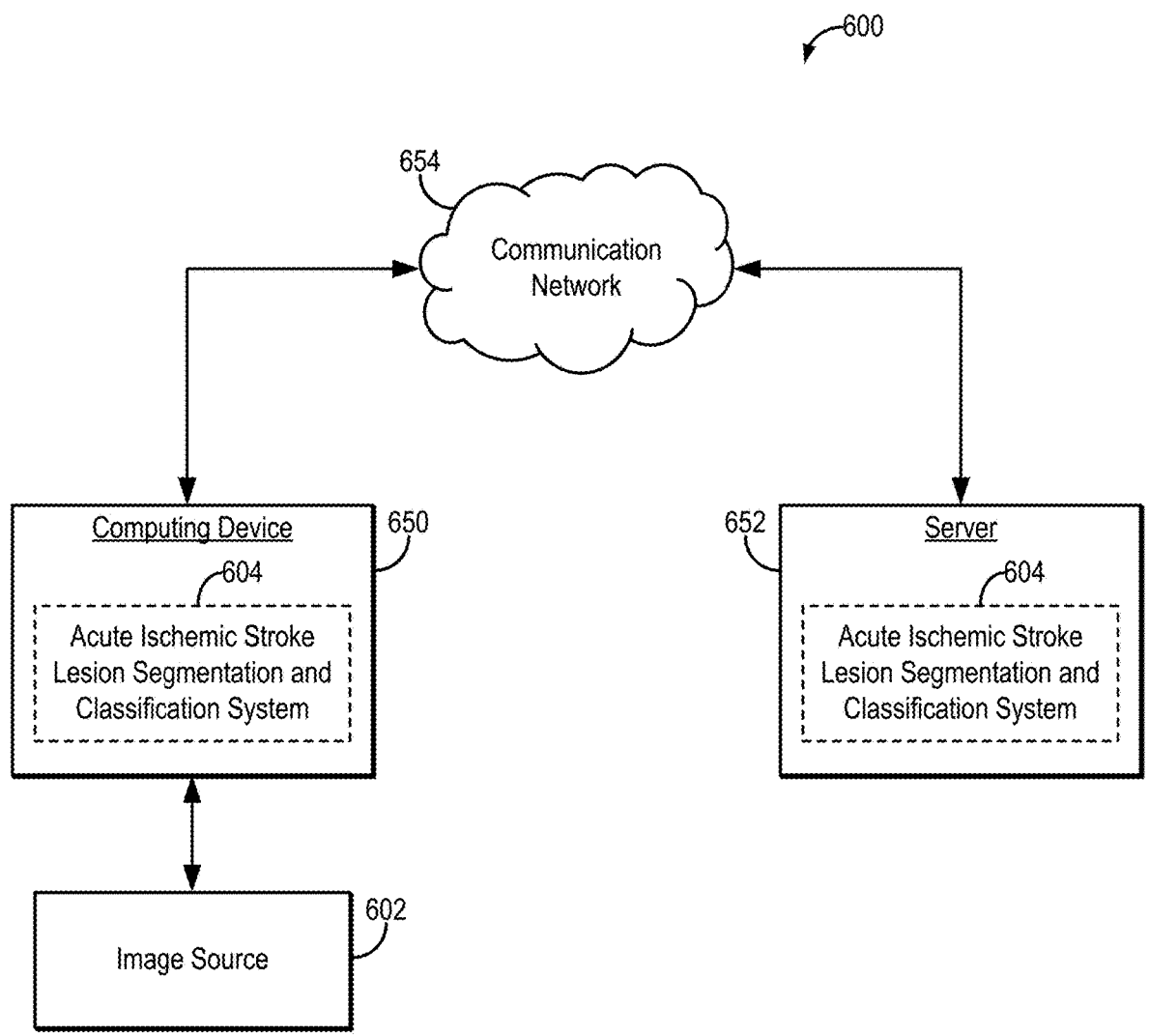
FIG. 6 is a block diagram of an example system for automatically segmenting and classifying acute ischemic stroke lesions.

Referring now to FIG. 6, an example of a system 600 for automatically segmenting and quantifying acute ischemic lesions using CT data in accordance with some embodiments of the systems and methods described in the present disclosure is shown. As shown in FIG. 6, a computing device 650 can receive one or more types of data (e.g., non-contrast CT data, CTA data, CTA-SI data, diffusion-weighted MRI data and/or labeled data generated from diffusion-weighted MRI data) from image source 602. In some embodiments, computing device 650 can execute at least a portion of an automatic acute ischemic stroke lesion segmentation and classification system 604 to automatically determine whether lesions are present in CT data of a subject's brain.

Additionally or alternatively, in some embodiments, the computing device 650 can communicate information about data received from the image source 602 to a server 652 over a communication network 654, which can execute at least a portion of the automatic acute ischemic stroke lesion segmentation and classification system 604. In such embodiments, the server 652 can return information to the computing device 650 (and/or any other suitable computing device) indicative of an output of the automatic acute ischemic stroke lesion segmentation and classification system 604.

In some embodiments, computing device 650 and/or server 652 can be any suitable computing device or combination of devices, such as a desktop computer, a laptop computer, a smartphone, a tablet computer, a wearable computer, a server computer, a virtual machine being executed by a physical computing device, and so on. The computing device 650 and/or server 652 can also reconstruct images from the data.

In some embodiments, image source 602 can be any suitable source of image data (e.g., measurement data, images reconstructed from measurement data), such as a CT system, an MRI system, another computing device (e.g., a server storing image data), and so on. In some embodiments, image source 602 can be local to computing device 650. For example, image source 602 can be incorporated with computing device 650 (e.g., computing device 650 can be configured as part of a device for capturing, scanning, and/or storing images). As another example, image source 602 can be connected to computing device 650 by a cable, a direct wireless link, and so on. Additionally or alternatively, in some embodiments, image source 602 can be located locally and/or remotely from computing device 650, and can communicate data to computing device 650 (and/or server 652) via a communication network (e.g., communication network 654).

In some embodiments, communication network 654 can be any suitable communication network or combination of communication networks. For example, communication network 654 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 654 can be a local area network, a wide area network, a public network (e.g., the Internet), a private or semi-private network (e.g., a corporate or university intranet), any other suitable type of network, or any suitable combination of networks. Communications links shown in FIG. 6 can each be any suitable communications link or combination of communications links, such as wired links, fiber optic links, Wi-Fi links, Bluetooth links, cellular links, and so on.

Figure 7:
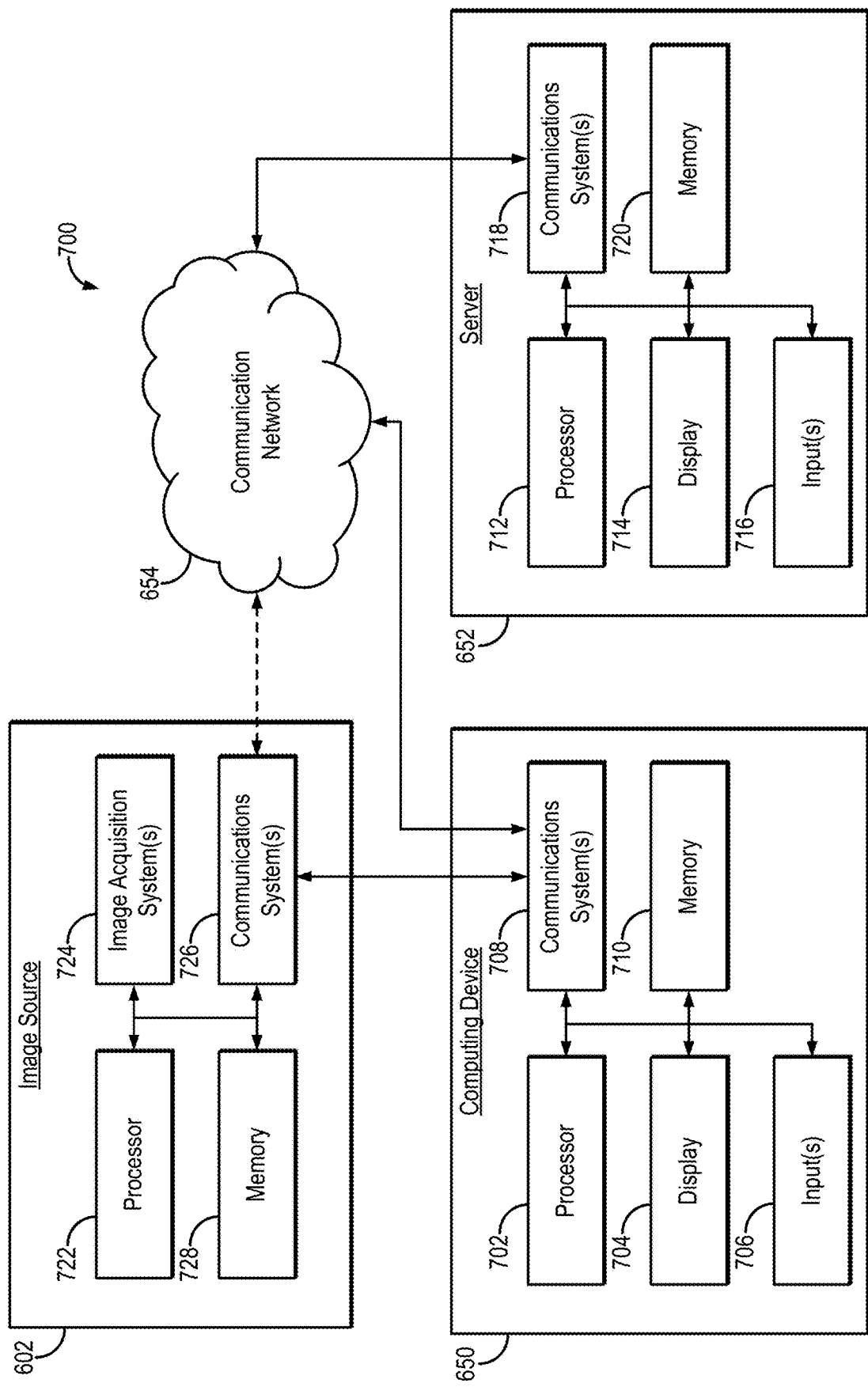
FIG. 7 is a block diagram showing example components of the system of FIG. 6.

Referring now to FIG. 7, an example of hardware 700 that can be used to implement image source 602, computing device 650, and server 652 in accordance with some embodiments of the systems and methods described in the present disclosure is shown. As shown in FIG. 7, in some embodiments, computing device 650 can include a processor 702, a display 704, one or more inputs 706, one or more communication systems 708, and/or memory 710. In some embodiments, processor 702 can be any suitable hardware processor or combination of processors, such as a central processing unit ("CPU"), a graphics processing unit ("GPU"), and so on. In some embodiments, display 704 can include any suitable display devices, such as a computer monitor, a touchscreen, a television, and so on. In some embodiments, inputs 706 can include any suitable input devices and/or sensors that can be used to receive user input, such as a keyboard, a mouse, a touchscreen, a microphone, and so on.

In some embodiments, communications systems 708 can include any suitable hardware, firmware, and/or software for communicating information over communication network 654 and/or any other suitable communication networks. For example, communications systems 708 can include one or more transceivers, one or more communication chips and/or chip sets, and so on. In a more particular example, communications systems 708 can include hardware, firmware and/or software that can be used to establish a Wi-Fi connection, a Bluetooth connection, a cellular connection, an Ethernet connection, and so on.

In some embodiments, memory 710 can include any suitable storage device or devices that can be used to store instructions, values, data, or the like, that can be used, for example, by processor 702 to present content using display 704, to communicate with server 652 via communications system(s) 708, and so on. Memory 710 can include any suitable volatile memory, non-volatile memory, storage, or any suitable combination thereof. For example, memory 710 can include RAM, ROM, EEPROM, one or more flash drives, one or more hard disks, one or more solid state drives, one or more optical drives, and so on. In some embodiments, memory 710 can have encoded thereon, or otherwise stored therein, a computer program for controlling operation of computing device 650. In such embodiments, processor 702 can execute at least a portion of the computer program to present content (e.g., images, user interfaces, graphics, tables), receive content from server 652, transmit information to server 652, and so on.

In some embodiments, server 652 can include a processor 712, a display 714, one or more inputs 716, one or more communications systems 718, and/or memory 720. In some embodiments, processor 712 can be any suitable hardware processor or combination of processors, such as a CPU, a GPU, and so on. In some embodiments, display 714 can include any suitable display devices, such as a computer monitor, a touchscreen, a television, and so on. In some embodiments, inputs 716 can include any suitable input devices and/or sensors that can be used to receive user input, such as a keyboard, a mouse, a touchscreen, a microphone, and so on.

In some embodiments, communications systems 718 can include any suitable hardware, firmware, and/or software for communicating information over communication network 654 and/or any other suitable communication networks. For example, communications systems 718 can include one or more transceivers, one or more communication chips and/or chip sets, and so on. In a more particular example, communications systems 718 can include hardware, firmware and/or software that can be used to establish a Wi-Fi connection, a Bluetooth connection, a cellular connection, an Ethernet connection, and so on.

In some embodiments, memory 720 can include any suitable storage device or devices that can be used to store instructions, values, data, or the like, that can be used, for example, by processor 712 to present content using display 714, to communicate with one or more computing devices 650, and so on. Memory 720 can include any suitable volatile memory, non-volatile memory, storage, or any suitable combination thereof. For example, memory 720 can include RAM, ROM, EEPROM, one or more flash drives, one or more hard disks, one or more solid state drives, one or more optical drives, and so on. In some embodiments, memory 720 can have encoded thereon a server program for controlling operation of server 652. In such embodiments, processor 712 can execute at least a portion of the server program to transmit information and/or content (e.g., data, images, a user interface) to one or more computing devices 650, receive information and/or content from one or more computing devices 650, receive instructions from one or more devices (e.g., a personal computer, a laptop computer, a tablet computer, a smartphone), and so on.

In some embodiments, image source 602 can include a processor 722, one or more image acquisition systems 724, one or more communications systems 726, and/or memory 728. In some embodiments, processor 722 can be any suitable hardware processor or combination of processors, such as a CPU, a GPU, and so on. In some embodiments, the one or more image acquisition systems 724 are generally configured to acquire data, images, or both, and can include a CT system and/or an MRI system. Additionally or alternatively, in some embodiments, one or more image acquisition systems 724 can include any suitable hardware, firmware, and/or software for coupling to and/or controlling operations of a CT system and/or an MRI system. In some embodiments, one or more portions of the one or more image acquisition systems 724 can be removable and/or replaceable.

Note that, although not shown, image source 602 can include any suitable inputs and/or outputs. For example, image source 602 can include input devices and/or sensors that can be used to receive user input, such as a keyboard, a mouse, a touchscreen, a microphone, a trackpad, a trackball, and so on. As another example, image source 602 can include any suitable display devices, such as a computer monitor, a touchscreen, a television, etc., one or more speakers, and so on.

In some embodiments, communications systems 726 can include any suitable hardware, firmware, and/or software for communicating information to computing device 650 (and, in some embodiments, over communication network 654 and/or any other suitable communication networks). For example, communications systems 726 can include one or more transceivers, one or more communication chips and/or chip sets, and so on. In a more particular example, communications systems 726 can include hardware, firmware and/ or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 728 can include any suitable storage device or devices that can be used to store instructions, values, data, or the like, that can be used, for example, by processor 722 to control the one or more image acquisition systems 724, and/or receive data from the one or more image acquisition systems 724; to images from data; present content (e.g., images, a user interface) using a display; communicate with one or more computing devices 650; and so on. Memory 728 can include any suitable volatile memory, non-volatile memory, storage, or any suitable combination thereof. For example, memory 728 can include RAM, ROM, EEPROM, one or more flash drives, one or more hard disks, one or more solid state drives, one or more optical drives, and so on. In some embodiments, memory 728 can have encoded thereon, or otherwise stored therein, a program for controlling operation of image source 602. In such embodiments, processor 722 can execute at least a portion of the program to generate images, transmit information and/or content (e.g., data, images) to one or more computing devices 650, receive information and/or content from one or more computing devices 650, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

The present disclosure has described one or more preferred embodiments, and it should be appreciated that many equivalents, alternatives, variations, and modifications, aside from those expressly stated, are possible and within the scope of the invention.

The invention claimed is:

1. A method for automatically generating a segmented image of an acute stroke patient using computed tomography (CT) data, the method comprising:
   (a) accessing CT data of a subject;
   (b) accessing a trained machine learning algorithm with a computer system, wherein the trained machine learning algorithms has been trained using labeled data and associated CT imaging data in order to segment acute ischemic stroke lesions, wherein the labeled data are generated based on diffusion-weighted magnetic resonance images;
   (c) generating segmented CT data with the computer system by inputting the CT data to the trained machine learning algorithm, generating output as the segmented CT data; and
   (d) displaying the segmented CT data to a user.

2. The method of claim 1, wherein the machine learning algorithm is a neural network.

3. The method of claim 2, wherein the neural network is a convolutional neural network (CNN).

4. The method of claim 1, wherein the labeled data comprise segmented lesion data indicating lesions that have been segmented from the diffusion weighted magnetic resonance images.

5. The method of claim 4, wherein the lesions are segmented from the diffusion-weighted magnetic resonance images manually by a user.

6. The method of claim 4, wherein the lesions are segmented from the diffusion-weighted magnetic resonance images automatically.

7. The method of claim 6, wherein the lesions are segmented from the diffusion-weighted magnetic resonance images by inputting the diffusion-weighted magnetic resonance images to a trained machine learning algorithm, generating output as the segmented data.

8. The method as recited in claim 4, wherein the diffusion-weighted magnetic resonance images are acquired within a time window from when the associated CT imaging data were acquired.

9. The method as recited in claim 8, wherein the time window is less than twenty-four hours.

10. The method as recited in claim 9, wherein the time window is less than one hour.

11. The method as recited in claim 1, wherein the associated CT imaging data used to train the machine learning algorithm comprise both non-contrast CT data and CT angiography source image (CTA-SI) data.

12. The method as recited in claim 1, wherein the CT data accessed with the computer system and input to the trained machine learning algorithm comprise both non-contrast CT data and CT angiography source image (CTA-SI) data.

13. The method of claim 1, wherein displaying the segmented CT data includes indicating an area of acute infract on an image of the subject corresponding to the CT data.

14. The method of claim 1, further comprising determining an efficacy of revascularization treatments for the subject using the segmented CT data.

15. The method of claim 1, further comprising generating output as infarct probability maps by inputting the CT data to the trained machine learning algorithm, generating output as the infarct probability maps, wherein the trained machine learning algorithm comprises a first output channel that generates output as the segmented CT data and a second output channel that generates output as the infarct probability maps.

\* \* \* \* \*